(12) United States Patent
 Pepper (10) Patent No.: US 9,259,559 B2
(45) Date of Patent: Feb. 16, 2016

(54) BALLOON CATHETER PRESSURE RELIEF VALVE

(71) Applicant: FUTUREMATRIX INTERVENTIONAL, INC., Athens, TX (US)

(72) Inventor: Lanny R. Pepper, Athens, TX (US)

(73) Assignee: FUTUREMATRIX INTERVENTIONAL, INC., Athens, TX (US)

(*) Notice: Subject to any disclaimer, the term of this patent is extended or adjusted under 35 U.S.C. 154(b) by 0 days.

(21) Appl. No.: 14/616,328

(22) Filed: Feb. 6, 2015

(65) Prior Publication Data
US 2015/0231378 A1    Aug. 20, 2015

Related U.S. Application Data

(63) Continuation-in-part of application No. 14/468,882, filed on Aug. 26, 2014, now abandoned, which is a continuation of application No. 12/390,573, filed on Feb. 23, 2009, now Pat. No. 8,814,899.

(51) Int. Cl.
 *A61M 29/00* (2006.01)
 *A61M 29/02* (2006.01)
 *A61M 25/10* (2013.01)

(52) U.S. Cl.
 CPC ......... *A61M 29/02* (2013.01); *A61M 25/10184* (2013.11); *A61M 25/104* (2013.01)

(58) Field of Classification Search
 CPC ... A61M 25/104; A61M 29/02; A61M 25/10; A61M 25/10184; A61B 17/12109; A61B 17/12136
 USPC ......... 606/191, 194; 604/96.01, 97.01, 99.01, 604/99.02, 99.04, 137; 251/61, 61.1; 137/14, 68, 19, 68.23
 See application file for complete search history.

(56) References Cited

U.S. PATENT DOCUMENTS

| | | | |
|---|---|---|---|
| 1,596,284 | A | 8/1926 | Malmgren |
| 2,043,083 | A | 6/1936 | Wappler |
| 3,769,981 | A | 11/1973 | McWhorter |

(Continued)

OTHER PUBLICATIONS

Nylon; Wikipedia, the free encyclopedia; Jun. 27, 2008; pp. 1-7; available at http://en.wikipedia.org/wiki/Nylon.

(Continued)

*Primary Examiner* — Tuan V Nguyen
*Assistant Examiner* — Kevin Everage
(74) *Attorney, Agent, or Firm* — Howison & Arnott, LLP (57) ABSTRACT

A pressure relief apparatus for a balloon dilation catheter having a shaft with a dilation balloon attached to the distal end of the shaft and an inflation/deflation lumen for inflating and deflating the balloon includes a pressure relief port formed through the wall of the inflation/deflation lumen with a pressure relief member secured across the pressure relief port to form a fluid tight seal such that the fluid tight seal formed by the pressure relief member fails at a predetermined pressure to release pressure from the inflation/deflation lumen through the pressure relief port. A splash guard is positioned across the pressure relief port, the splash guard being formed from a fluid permeable body defining a plurality of flow passages therethrough, whereby the splash guard partially obstructs fluid flow through the pressure relief port to prevent a direct uncontrolled release of the fluid from the pressure relief port.

19 Claims, 8 Drawing Sheets

(56) References Cited

U.S. PATENT DOCUMENTS

| | | |
|---|---|---|
| 3,981,415 A | 9/1976 | Fowler et al. |
| 4,367,396 A | 1/1983 | Ravinsky |
| 4,482,516 A | 11/1984 | Bowman et al. |
| 4,572,186 A | 2/1986 | Gould et al. |
| 4,637,396 A | 1/1987 | Cook |
| 4,652,258 A | 3/1987 | Drach |
| 4,702,252 A | 10/1987 | Brooks |
| 4,704,130 A | 11/1987 | Gilding et al. |
| 4,706,670 A | 11/1987 | Andersen et al. |
| 4,748,982 A | 6/1988 | Horzewski et al. |
| 4,796,629 A | 1/1989 | Grayzel |
| 4,834,755 A | 5/1989 | Silvestrini et al. |
| 4,884,573 A | 12/1989 | Wijay et al. |
| 4,952,357 A | 8/1990 | Euteneuer |
| 4,983,167 A | 1/1991 | Sahota |
| 4,998,421 A | 3/1991 | Zafiroglu |
| 5,042,985 A | 8/1991 | Elliott et al. |
| 5,046,497 A | 9/1991 | Millar |
| 5,061,273 A | 10/1991 | Yock |
| 5,078,727 A | 1/1992 | Hannam et al. |
| 5,108,415 A | 4/1992 | Pinchuk et al. |
| 5,112,304 A | 5/1992 | Barlow et al. |
| 5,116,360 A | 5/1992 | Pinchuk et al. |
| 5,171,297 A | 12/1992 | Barlow et al. |
| 5,201,706 A | 4/1993 | Noguchi et al. |
| 5,207,700 A | 5/1993 | Euteneuer |
| 5,264,260 A | 11/1993 | Saab |
| 5,270,086 A | 12/1993 | Hamlin |
| 5,290,306 A | 3/1994 | Trotta et al. |
| 5,295,960 A | 3/1994 | Aliahmad et al. |
| 5,304,340 A | 4/1994 | Downey |
| 5,306,245 A | 4/1994 | Heaven |
| 5,306,246 A | 4/1994 | Sahatjian et al. |
| 5,314,443 A | 5/1994 | Rudnick |
| 5,330,429 A | 7/1994 | Noguchi et al. |
| 5,338,299 A | 8/1994 | Barlow |
| 5,344,401 A | 9/1994 | Radisch et al. |
| 5,358,486 A | 10/1994 | Saab |
| 5,410,797 A | 5/1995 | Steinke et al. |
| 5,451,209 A | 9/1995 | Ainsworth et al. |
| 5,451,233 A | 9/1995 | Yock |
| 5,464,394 A | 11/1995 | Miller et al. |
| 5,470,314 A | 11/1995 | Wallinsky |
| 5,477,886 A | 12/1995 | Van Beugen et al. |
| 5,478,320 A | 12/1995 | Trotta |
| 5,492,532 A | 2/1996 | Ryan et al. |
| 5,755,690 A | 5/1996 | Saab |
| 5,549,552 A | 8/1996 | Peters et al. |
| 5,549,556 A | 8/1996 | Ndondo-Lay et al. |
| 5,554,120 A | 9/1996 | Chen et al. |
| 5,575,771 A | 11/1996 | Walinsky |
| 5,587,125 A | 12/1996 | Roychowdhury |
| 5,599,576 A | 2/1997 | Opolski |
| 5,620,649 A | 4/1997 | Trotta |
| 5,647,848 A | 7/1997 | Jørgensen |
| 5,690,642 A | 11/1997 | Osborne et al. |
| 5,728,063 A | 3/1998 | Preissman et al. |
| 5,741,325 A | 4/1998 | Chaikof et al. |
| 5,752,934 A | 5/1998 | Campbell et al. |
| 5,759,172 A | 6/1998 | Weber et al. |
| 5,769,817 A | 6/1998 | Burgmeier |
| 5,772,681 A | 6/1998 | Leoni |
| 5,788,979 A | 8/1998 | Alt et al. |
| 5,797,877 A | 8/1998 | Hamilton et al. |
| 5,820,613 A | 10/1998 | Van Werven-Fransesen et al. |
| 5,868,779 A | 2/1999 | Ruiz |
| 5,879,369 A | 3/1999 | Ishida |
| 5,928,181 A | 7/1999 | Coleman et al. |
| 5,972,441 A | 10/1999 | Campbell et al. |
| 5,980,486 A | 11/1999 | Enger |
| 6,007,544 A | 12/1999 | Kim |
| 6,010,480 A | 1/2000 | Abele et al. |
| 6,012,457 A | 1/2000 | Lesh |
| 6,015,430 A | 1/2000 | Wall |
| 6,024,740 A | 2/2000 | Lesh et al. |
| 6,024,772 A | 2/2000 | Nishiyama et al. |
| 6,027,779 A | 2/2000 | Campbell et al. |
| 6,036,697 A | 3/2000 | DiCaprio |
| 6,036,715 A | 3/2000 | Yock |
| 6,117,101 A | 9/2000 | Diederich et al. |
| 6,124,007 A | 9/2000 | Wang et al. |
| 6,127,597 A | 10/2000 | Beyar et al. |
| 6,129,708 A | 10/2000 | Enger |
| 6,156,254 A | 12/2000 | Andrews et al. |
| 6,159,238 A | 12/2000 | Killion et al. |
| 6,164,283 A | 12/2000 | Lesh |
| 6,171,297 B1 | 1/2001 | Pedersen et al. |
| 6,183,492 B1 | 2/2001 | Hart et al. |
| 6,186,978 B1 | 2/2001 | Samson et al. |
| 6,187,013 B1 | 2/2001 | Stollze et al. |
| 6,213,995 B1 | 4/2001 | Steen et al. |
| 6,234,995 B1 | 5/2001 | Peacock, III |
| 6,245,064 B1 | 6/2001 | Lesh et al. |
| 6,254,599 B1 | 7/2001 | Lesh et al. |
| 6,263,236 B1 | 7/2001 | Kasinkas et al. |
| 6,270,902 B1 | 8/2001 | Tedeschi et al. |
| 6,290,485 B1 | 9/2001 | Wang |
| 6,305,378 B1 | 10/2001 | Lesh |
| 6,306,154 B1 | 10/2001 | Hudson et al. |
| 6,309,379 B1 | 10/2001 | Willard et al. |
| 6,315,751 B1 | 11/2001 | Cosgrove et al. |
| 6,328,925 B1 | 12/2001 | Wang et al. |
| 6,361,529 B1 | 3/2002 | Goodin et al. |
| 6,394,995 B1 | 5/2002 | Solar et al. |
| 6,544,219 B2 | 4/2003 | Happ et al. |
| 6,626,889 B1 | 9/2003 | Simpson et al. |
| 6,663,648 B1 | 12/2003 | Trotta |
| 6,702,750 B2 | 3/2004 | Yock |
| 6,702,782 B2 | 3/2004 | Miller et al. |
| 6,706,051 B2 | 3/2004 | Hudson et al. |
| 6,733,487 B2 | 5/2004 | Keith et al. |
| 6,743,196 B2 | 6/2004 | Barbut et al. |
| 6,746,425 B1 | 6/2004 | Beckham |
| 6,755,845 B2 | 6/2004 | Kieturakis et al. |
| 6,761,708 B1 | 7/2004 | Chiu et al. |
| 6,899,713 B2 | 5/2005 | Shaolian et al. |
| 6,905,743 B1 | 6/2005 | Chen et al. |
| 6,911,038 B2 | 6/2005 | Mertens et al. |
| 6,942,680 B2 | 9/2005 | Grayzel et al. |
| 6,977,103 B2 | 12/2005 | Chen et al. |
| 7,252,650 B1 | 8/2007 | Andrews et al. |
| 7,300,415 B2 | 11/2007 | McMurtry et al. |
| 7,309,324 B2 | 12/2007 | Hayes et al. |
| 7,354,419 B2 | 4/2008 | Davies et al. |
| 7,435,254 B2 | 10/2008 | Chouinard et al. |
| 7,500,982 B2 | 3/2009 | Pepper |
| 7,544,201 B2 | 6/2009 | Pepper |
| 7,635,510 B2 | 12/2009 | Horn et al. |
| 7,662,163 B2 | 2/2010 | Grayzel et al. |
| 7,682,335 B2 | 3/2010 | Pepper et al. |
| 2002/0058960 A1 | 5/2002 | Hudson et al. |
| 2002/0077653 A1 | 6/2002 | Hudson et al. |
| 2002/0161388 A1 | 10/2002 | Samuels et al. |
| 2004/0015182 A1 | 1/2004 | Kieturakis et al. |
| 2004/0039332 A1 | 2/2004 | Kantor |
| 2004/0073163 A1 | 4/2004 | Tomaschko et al. |
| 2004/0073299 A1 | 4/2004 | Hudson et al. |
| 2004/0082965 A1 | 4/2004 | Beckham |
| 2004/0109964 A1 | 6/2004 | Beckham |
| 2004/0176740 A1 | 9/2004 | Chouinard |
| 2005/0027249 A1 | 2/2005 | Reifart et al. |
| 2005/0033225 A1 | 2/2005 | Wu et al. |
| 2005/0102020 A1 | 5/2005 | Grayzel et al. |
| 2005/0121073 A1* | 6/2005 | Carroll .................. F16K 17/16 137/68.23 |
| 2005/0123702 A1 | 6/2005 | Beckham |
| 2005/0267408 A1 | 12/2005 | Grandt et al. |
| 2005/0271844 A1 | 12/2005 | Mapes et al. |
| 2006/0015133 A1 | 1/2006 | Grayzel et al. |
| 2006/0085022 A1 | 4/2006 | Hayes et al. |
| 2006/0085023 A1 | 4/2006 | Davies et al. |
| 2006/0085024 A1 | 4/2006 | Pepper et al. |
| 2007/0010847 A1 | 1/2007 | Pepper |
| 2007/0016133 A1 | 1/2007 | Pepper |

(56) References Cited

U.S. PATENT DOCUMENTS

| | | |
|---|---|---|
| 2007/0059466 A1 | 3/2007 | Beckham |
| 2007/0093865 A1 | 4/2007 | Beckham |
| 2007/0213760 A1 | 9/2007 | Hayes et al. |
| 2007/0219490 A1 | 9/2007 | Pepper et al. |
| 2008/0009793 A1* | 1/2008 | Dabbs ............ A61M 25/10 604/99.04 |
| 2008/0082050 A1 | 4/2008 | Solar et al. |
| 2008/0183132 A1 | 7/2008 | Davies et al. |
| 2008/0188805 A1 | 8/2008 | Davies et al. |
| 2008/0255507 A1 | 10/2008 | Mushtaha |
| 2009/0043254 A1 | 2/2009 | Pepper et al. |
| 2009/0171277 A1 | 7/2009 | Pepper |
| 2009/0247947 A1 | 10/2009 | Pepper |
| 2009/0294031 A1 | 12/2009 | Pepper et al. |

OTHER PUBLICATIONS

Fiber; Wikipedia, the free encyclopedia; Jun. 27, 2008; pp. 1-3; available at http://en.wikipedia.org/wiki/Fiber.

Putnam Plastics Corporation; Putnam Plastics—Thermoset Polyimide Tubing; Mar. 20, 2005; available at www.putnamplastics.com.

Arkema Group; Pebax® Application Areas; Jun. 2000.

* cited by examiner

BALLOON CATHETER PRESSURE RELIEF VALVE

CROSS-REFERENCE TO RELATED APPLICATIONS

This application is a Continuation-In-Part of U.S. patent application Ser. No. 14/468,882, filed Aug. 26, 2014, entitled BALLOON CATHETER PRESSURE RELIEF VALVE, published as U.S. Patent Application Publication No. US 2014-0364893 A1. U.S. patent application Ser. No. 14/468,882 is a continuation of U.S. patent application Ser. No. 12/390,573, filed Feb. 23, 2009, entitled BALLOON CATHETER PRESSURE RELIEF VALVE, published as U.S. Patent Application Publication No. US 2010-0217189 A1, now U.S. Pat. No. 8,814,899, issued Aug. 26, 2014. U.S. Pat. No. 8,814,899 and U.S. Patent Application Publication Nos. US 2014-0364893 A1 and 2010-0217189 A1 are hereby incorporated by reference herein.

TECHNICAL FIELD

The disclosure relates to dilation balloon catheters and, in particular, dilation balloon catheters having a pressure relief valve for limiting the amount of pressure that may be applied to the balloon.

BACKGROUND

Angioplasty is the technique of mechanical widening a narrowed or totally obstructed blood vessel; typically as a result of atherosclerosis. A catheter is used to maneuver a tightly folded balloon attached to the distal end of the catheter into the narrowed location (stenosis). An incompressible fluid is then pumped through the catheter to inflate the balloon and enlarge the narrowed portion of the blood vessel. Relatively high pressures, in some instances up to 30 atmospheres, may be used to inflate the balloon. After the procedure is complete, a negative pressure may be applied through the catheter to remove the incompressible fluid, deflating the balloon for removal from the blood vessel.

Catheter dilation balloons are typically provided with a rated operating pressure and a rated burst pressure. The rated operating pressure is the pressure at which the balloon reaches its nominal diameter. The rated burst pressure is a statistical measure, e.g., typically a maximum pressure at which there is a 95% confidence level that 99.99% of balloons will not fail. Non-compliant catheter balloons are typically used at pressures between the rated operating pressure and the rated burst pressure.

However, due to the high pressures used in many cases to inflate a dilation catheter balloon during angioplasty and the relatively small volume of the balloons used, there is a potential to pressurize a dilation balloon beyond its rated burst pressure. Further, in some instances a dilation catheter balloon may be inflated and deflated multiple times during angioplasty, weakening the balloon. If a balloon bursts during angioplasty, there is a possibility that portions of the balloon may separate from the catheter, possibly necessitating surgery to remove the separated portions of the balloon from the patient's artery. Thus, there exists a need for a means of preventing over-inflation of dilation balloons during procedures such as angioplasty.

SUMMARY

In one aspect thereof, a pressure relief apparatus for a balloon dilation catheter is provided. The balloon dilation catheter includes a shaft having a dilation balloon attached to the distal end of the shaft, an inflation/deflation lumen for inflating and deflating the balloon and a pressure relief port formed through the wall of the inflation/deflation lumen. A pressure relief member is secured across the pressure relief port to form a fluid tight seal. The fluid tight seal is configured to fail (e.g. burst, rupture, tear or leak) at a predetermined pressure to release pressure from the inflation/deflation lumen through the pressure relief port. The predetermined pressure may be greater than or equal to the rated burst pressure of the dilation balloon.

In one variation, the pressure relief port comprises a first outwardly opening passage and a second passage in fluid communication with the first passage. The second passage extends inwardly from the first passage and opens into the inflation/deflation lumen. In this variation, the cross-sectional area of the first passage may be larger than the cross-sectional area of the second passage.

In one embodiment, a wall extends radially between an inside end of the first passage of the pressure relief port and an outside end of the second passage of the pressure relief port. The pressure relief member may be disposed adjacent the wall and across the outside end of the second passage of the pressure relief port to block the pressure relief port and form a fluid tight seal. The pressure relief member may be a plastic film, a thin metallic film or a similar material. A retainer for retaining the pressure relief member in the pressure relief port may be utilized such that the pressure relief member and retainer form a fluid tight seal across the pressure relief port.

In another aspect, a pressure relief apparatus for a dilation catheter having a balloon with a rated burst pressure includes a hub adapted for connection to a proximal end portion of a balloon dilation catheter shaft wherein a pressure relief port is formed in the hub. In one embodiment, the hub may comprise a plastic a body that defines an inflation/deflation lumen and a guidewire lumen.

The hub may be formed from a substantially rigid material and includes a wall defining the inflation/deflation lumen for directing a substantially incompressible inflation medium into and from an inflation/deflation lumen of the catheter shaft. The hub includes a pressure relief port formed through the wall of the hub and a pressure relief member disposed across the pressure relief port to form a fluid tight seal across the pressure relief port. The pressure relief member is configured to fail, (e.g. rupture, tear, burst or leak), at a predetermined pressure to release pressure from the inflation/deflation port through the pressure relief port.

In one configuration, the relief port includes a first outwardly opening passage and a second passage in fluid communication with the first passage. The second passage extends inwardly from the first passage and opens into the inflation lumen of the hub. A wall extends radially between an inside end of the first passage of the pressure relief port and an outside end of the second passage of the pressure relief port. In this variation, the pressure relief member may be disposed adjacent the wall and across the outermost end of the second passage of the pressure relief port. The pressure relief member may be secured against the wall and across the outside end of the second passage with a retainer positioned in the first passage whereby the pressure relief member and retainer form a fluid tight seal across the pressure relief port.

In another aspect, a dilation catheter having a pressure relief apparatus includes a catheter shaft having a proximal end portion and a distal end portion with a dilation balloon having a rated burst pressure attached to the distal end portion of the catheter shaft. The catheter shaft includes an outer tubular member that forms an inflation/deflation lumen extending through the catheter shaft from adjacent the proximal end portion of the catheter shaft to the balloon such that the inflation/deflation lumen is in fluid communication with the balloon. A hub is connected to the proximal end portion of the catheter shaft. The hub may be formed from a substantially rigid material and has a wall defining an inflation/deflation lumen for directing a substantially incompressible inflation medium into and from the inflation/deflation lumen of the catheter shaft.

In one variation, the pressure relief apparatus includes a pressure relief port formed through the wall of the hub. The pressure relief port may include a first outwardly opening passage and a second passage in fluid communication with the first passage and extending inwardly from the first passage and opening into the inflation/deflation lumen. In one embodiment, the diameter and cross-sectional area of the first passage is larger than the diameter and cross-sectional area of the second passage. A pressure relief member may be disposed adjacent an annular wall that extends between an inside end of the first passage of the pressure relief port and an outside end of the second passage of the pressure relief port. The pressure relief member blocks the pressure relief port, forming a fluid tight seal at pressures less than the rated burst pressure of the balloon. A retainer positioned in the first passage may be utilized to retain the pressure relief member against the annular wall. In one variation, the pressure relief member is one or more layers of a plastic film, in other variations the pressure relief member may be a thin layer of metallic material.

In a different aspect, the pressure relief apparatus may incorporate a splash guard positioned across the pressure relief port to prevent an uncontrolled spurt of fluid from the pressure relief port upon a rupture or failure of the pressure relief member. The splash guard may be formed from a fluid permeable body such that fluid released from the inflation/deflation lumen upon failure of the pressure relief member impinges the splash guard which partially obstructs fluid flow through the pressure relief port to prevent a direct uncontrolled release or spurt of the fluid through the pressure relief port to the external environment.

The splash guard may be formed from a plastic or metal mesh material, and positioned inside the pressure relief port. The splash guard defines a plurality of relatively narrow (e.g. having a significantly smaller cross-sectional area than the first and second passages) fluid flow passages that impede the flow of fluid through the pressure relief port and decrease the pressure of the fluid thereby preventing an uncontrolled stream, spurt or spray of fluid from the port.

In one variation, the splash guard is positioned inside the pressure relief port with a portion thereof extending outwardly from the pressure relief port. In another variation the pressure relief member comprises a fluid permeable fabric material extending around at least a portion of the periphery of the wall of the inflation/deflation lumen and over the pressure relief port. In yet another variation, the splash guard may comprise sheet material that is perforated, coiled, folded or positioned partially across the pressure relief port so as to change the direction of fluid flowing though the pressure relief port. The splash guard reduces the velocity of fluid flowing through the pressure relief port and increases the pressure drop across the pressure relief port so as to prevent a direct, unobstructed linear release of fluid from the port.

In another variation, a pressure relief apparatus for a balloon dilation catheter includes an extension of the inflation/deflation lumen having a fluid inlet port and a fluid outlet port with a pressure relief port formed through a wall of the inflation/deflation lumen. The pressure relief port includes a first outwardly opening passage and a second passage in fluid communication with the first passage that extends inwardly from the first passage and opens into the inflation/deflation lumen with the cross-sectional area of the first passage being larger than the cross-sectional area of the second passage. An interior wall extends radially between an inside end of the first passage of the pressure relief port and an outside end of the second passage of the pressure relief port. A pressure relief member is secured to the interior wall and extends across the pressure relief port to form a fluid tight seal enabling inflation of the dilation balloon with a substantially incompressible fluid provided through the inflation/deflation lumen. The fluid tight seal formed by the pressure relief member is selected to fail when the pressure in the inflation/deflation lumen exceeds the predetermined pressure. One of fluid inlet port and fluid outlet port of the extension is configured with a male tapered cone fitting and the other of the fluid inlet port or fluid outlet port is configured with a female tapered cone fitting.

BRIEF DESCRIPTION OF THE DRAWINGS

For a more complete understanding, reference is now made to the following description taken in conjunction with the accompanying Drawings in which.

DETAILED DESCRIPTION

Referring now to the drawings, wherein like reference numbers are used herein to designate like elements throughout, the various views and embodiments of a balloon catheter pressure relief valve are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 1:
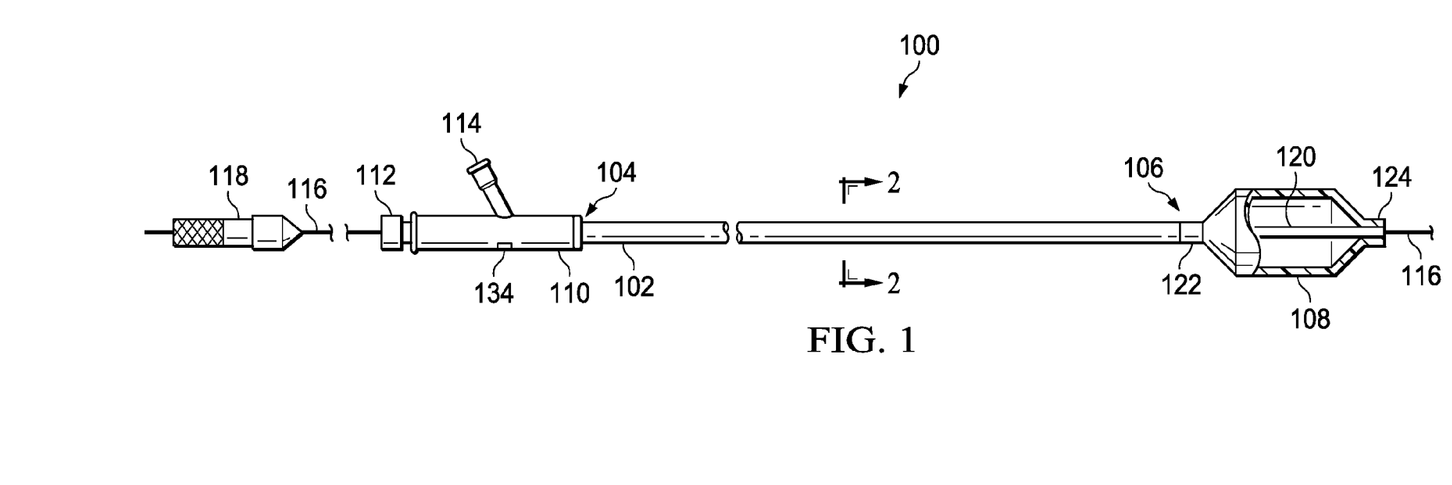
FIG. 1 illustrates a balloon dilation catheter according to the disclosure.

Turning now to FIG. 1 a balloon dilation catheter 100 includes a shaft 102 having a proximate end 104 and a distal end 106. In one variation, a plurality of tubular members disposed in catheter 100 define internal, longitudinally extending passages known as lumens. An access fitting or hub 110 is affixed to the proximal end of catheter shaft 102 to provide access to the lumens. One tubular member, the guidewire tubular member 120, extends longitudinally through the catheter from hub 110 to the distal end 124 of dilation balloon 108. The guidewire tubular member 120 has a bore defining a guidewire lumen through which a conventional guidewire 116 may be directed through the interior of catheter 100.

As illustrated, hub 110 includes a first port 112 for receiving guidewire 116 therethrough and directing the guidewire into the guidewire lumen in shaft 102. Hub 110 further includes a second inflation/deflation port 114 adapted to receive an incompressible inflation medium and direct the medium into an inflation/deflation lumen that extends through the hub and shaft 102. As illustrated, hub 110 includes a pressure relief port 134 that extends through the wall of the hub and into the inflation/deflation lumen of the hub. A manipulator 118 may be provided for rotating and positioning guidewire 116 from the proximal end of catheter 100.

Referring still to FIG. 1, the proximal end 122 of dilation balloon 108 is affixed to the distal end 106 of shaft 102. In the case of non-compliant balloons typically used in angioplasty, balloon 108 may be of conventional construction and is typically formed of relatively non-distensible plastic or polymer material such as nylon. Non-compliant balloons will typically expand less than about 10%, and more typically less than about 5%, when pressurized from the rated operating pressure to the balloon's rated burst pressure.

The envelope of balloon 108 may be plain or reinforced with filaments or fibers. For the purpose of illustration, balloon 108 is shown in an inflated configuration in FIG. 1 with portions of the balloon cut away to better to illustrate the interior structure of catheter 100. Although balloon 108 is illustrated in an inflated configuration, it will be appreciated that when deflated the balloon can typically be folded in such a manner as to have an outside diameter or cross section approximately equal to that of catheter shaft 102.

The proximate end 122 of balloon 108 may be attached to the distal end 106 of shaft 102 of shaft 102 using various techniques known in the art, for example with an appropriate adhesive such as medical grade epoxy adhesive. The distal end 124 of balloon 108 is connected with a fluid-tight seal to the outside (i.e. radial) surface of guidewire tubular member 120, which, as illustrated, extends beyond the distal end 106 of the catheter shaft 102, passing through the interior of balloon 108. The distal end 124 of balloon 108 may be welded to guidewire tubular member 120 or adhered to the guidewire tubular member with an appropriate adhesive to form a fluid-tight seal.

Figure 2:
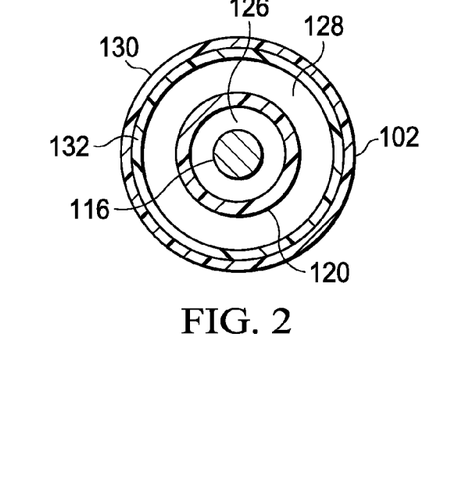
FIG. 2 is cross-sectional view of the shaft of the catheter of FIG. 1, taken along line 2-2 of FIG. 1.

FIG. 2 is a cross-sectional view of catheter shaft 102 taken along line 2-2 of FIG. 1. In one embodiment, catheter shaft 102 may have a coaxial configuration wherein guidewire tubular member 120 defines a guidewire lumen 126. An outer tubular member 132 extends coaxially with guidewire lumen 126 and defines an annular inflation/deflation lumen 128 between the inside surface of the outer tubular member and the outside surface of guidewire tubular member 120. Inflation/deflation lumen 128 extends from inflation/deflation port 114 of hub 110 to balloon 108, providing a fluid passageway for the incompressible fluid used to inflate the balloon. Catheter shaft 102 may include a coating 130 to increase the lubricity of the catheter shaft.

Outer tubular member 132 and guidewire tubular member 120 may be formed from a variety of suitable plastic materials such as nylon-11, nylon-12 and/or a polyether block amide (PEBA). In one embodiment, guidewire tubular member 120 and/or outer tubular member 132 may be formed from PEBA elastomers sold under the trademark Pebax®. PEBA elastomers are available in plasticizer and additive-free medical grades having a nominal hardness (Shore D) from about Shore D 30 to about Shore D 72. The thermoplastic materials used to make guidewire tubular member 120 and outer tubular member 132 may be loaded with materials such as carbon nanotubes or similar materials in order to enhance the strength of the tubular members. In other variations, guidewire tubular member 120 and/or outer tubular member 132 may be loaded with up to approximately twenty percent by weight of a radiopaque material such as bismuth.

Figures 3, 4:
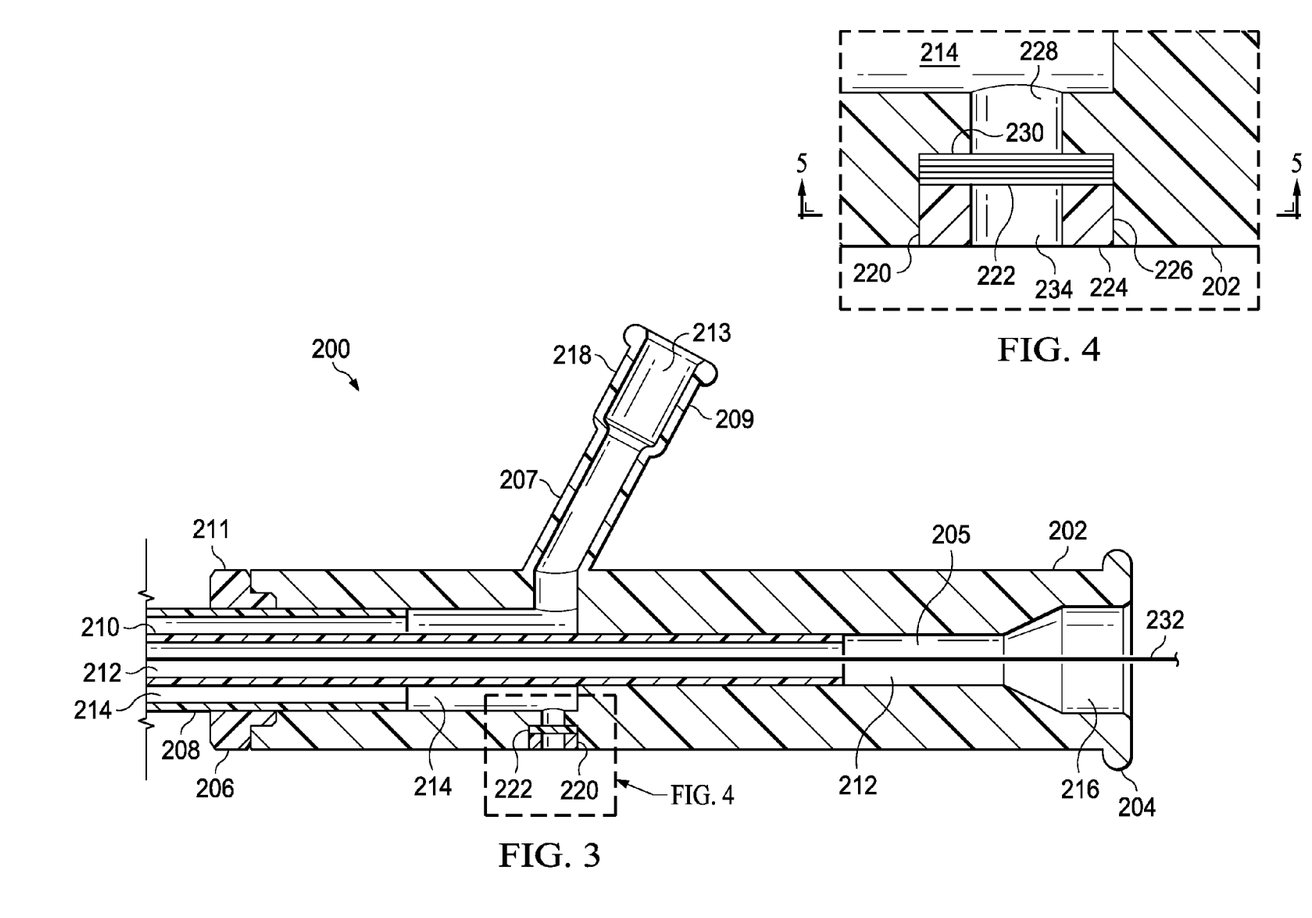
FIG. 3 is a length-wise section view of the hub of the balloon dilation catheter of FIG. 1.
FIG. 4 is an enlarged view of a portion of the sectional view of FIG. 3 further illustrating the pressure relief port.

FIG. 3 is a length wise sectional view of a hub 200 according to the disclosure. Hub 200 may be molded from an appropriate plastic such as nylon and includes a substantially rigid cylindrical wall 202 having a proximate end 204 and a distal end 206. In one embodiment hub 200 may include a separately molded end cap 211 that is glued into the distal end of the hub with an appropriate adhesive to facilitate assembly of the hub.

Cylindrical wall 202 defines a central passage 205 extending longitudinally through hub 200. An outer tubular member 208 of a catheter shaft may be inserted into the distal end passage 205 and secured to an inside surface of cylindrical wall 202 with an adhesive such as a medical grade epoxy to provide a fluid tight seal. A guidewire tubular member 210 is positioned inside outer tubular member 208. Guidewire tubular member 210 extends past the proximate end of the outer tubular member 208 and may be secured to the inside surface of cylindrical wall 202 with an appropriate adhesive to form a fluid tight seal. Guidewire tubular member 208 and the inside surface of cylindrical wall 202 proximate to the end of guidewire tubular member define a guidewire lumen 212 extending through hub 200. In one variation, an enlarged portion 216 of the proximate end of passage 205 serves as a guide for inserting or threading guidewire 232 into hub 200.

The inside surface of wall 202 and the outside surface of guidewire tubular member 210 define an annular inflation/deflation lumen 214 within hub 200 that extends distally from the location where guidewire tubular member 210 is sealed against the inside surface of wall 202. Inflation/deflation lumen 214 extends from hub 200 between the inside surface of the outer tubular member 208 and the outside surface of guidewire tubular member 210 to a dilation balloon such as balloon 108 of FIG. 1. Hub 200 includes an inflation/deflation port 218 through which an incompressible fluid (e.g. inflation medium) may be directed into and out of the hub. In one variation, inflation/deflation port 218 comprises a cylindrical wall 207 that may be integrally molded with wall 202. As illustrated, wall 207 defines a passageway 211 that opens into inflation/deflation lumen 214 at a location distal to the fluid tight seal between guidewire tubular member 210 and the inside surface of cylindrical wall 202. In the illustrated embodiment, cylindrical wall 207 includes an enlarged end 209 to facilitate connection of a source of pressurized fluid to hub 200.

Referring still to FIG. 3, a pressure relief port 220 is formed through cylindrical wall 202. Pressure relief port 220 opens into inflation/deflation lumen 214 and a pressure relief member 222 is secured across the pressure relief port to form a fluid tight seal. In one embodiment, pressure relief member 222 may be one or more layers of a suitable plastic film having a tensile strength such that film ruptures or tears when the pressure in inflation/deflation lumen 214 exceeds a predetermined value, for example a selected pressure between 6 and 30 atmospheres. The predetermined pressure value may be approximately equal to the rated burst pressure of a dilation balloon used with a catheter incorporating hub 200. In other variations, the predetermined value may be greater than or less than the rated burst pressure of the balloon.

FIG. 4 is an enlarged view of the encircled portion of FIG. 3 further illustrating relief port 220. As illustrated, relief port 220 includes an enlarged outwardly opening passage 226 and a smaller diameter inner passage 228 that opens into inflation/deflation lumen 214. An annular wall 230 extends radially between outwardly opening passage 226 and inner passage 228. As illustrated, pressure relief member 222 extends across inner passage 228 and annular wall 230. Pressure relief member 222 may be glued to annular wall 230 with an appropriate adhesive, such as a medical grade epoxy, to form a fluid-tight seal across relief port 220. In other embodiments, pressure relief member 222 may be solvent welded or thermally or ultrasonically welded in place. In one embodiment, a cylindrical retainer 224 is positioned in outwardly opening passage 226 over pressure relief member 222. In the embodiment shown in FIG. 4, pressure relief member 222 is positioned between retainer 224 and annular wall 228.

Figure 5:
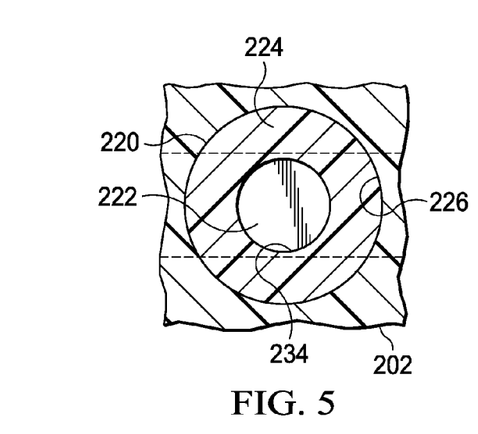
FIG. 5 is an end view of the pressure relief port of FIG. 4.

FIG. 5 is an enlarged end view of relief port 220. As illustrated, retainer 224 has an outside diameter approximately equal to the inside diameter of outwardly opening passage 226 and a centrally located cylindrical opening 234 having a diameter approximately equal to the diameter of inner passage 228 through which pressure relief member 222 is exposed. Retainer 224 may be secured in outwardly opening passage 226 and/or to pressure relief member 222 with an appropriate adhesive or by means of solvent, thermal or ultrasonic welding.

In the illustrated embodiments, relief port 220 has a generally circular configuration. However, in other embodiments relief port 220 may be rectangular, oval or polygonal. In other variations relief member 222 and retainer 224 may be formed as a single integral component by means of, for example, molding. In yet other embodiments, pressure relief member 222 may be scored or otherwise weakened in order to burst at a selected predetermined pressure. Although as illustrated, pressure relief member 222 is formed from one or more layers of a plastic film, it is contemplated that the relief member may be formed form other materials having the same or different geometries. For example, pressure relief member may be formed as a thin metal disk having a flat or curved cross-section.

Figure 6:
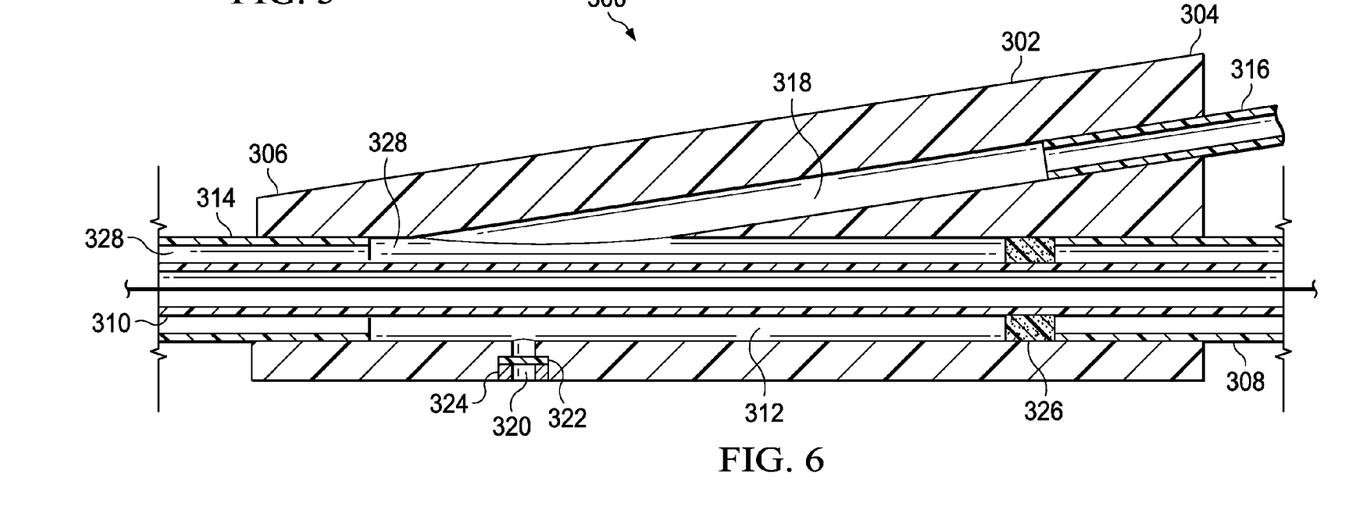
FIG. 6 is a length-wise section view of an alternate hub for use with a balloon dilation catheter.

Turning to FIG. 6, in an alternate embodiment, a catheter hub 300 comprises a substantially rigid, integrally formed body 302 having a proximate end 304 and a distal end 306. Body 302 may be molded from a suitable plastic such as nylon. A guidewire tubular member 310 passes through a longitudinally extending central passage 312 formed in body 302. A proximate portion of guidewire tubular member 310 is encased in a first outer tubular member 308 that extends into the proximate end of central passage 312. First outer tubular member 308 and guidewire tubular member 310 are secured in position in hub 300 with an adhesive 326 that forms a fluid tight seal between the guidewire tubular member and the inside surface of central passage 312. A second outer tubular member 314 is positioned over guidewire tubular member 310 and secured in central passage 312 at the distal end 306 of hub 300 with an appropriate adhesive or by means of thermal, solvent or ultrasonic welding. The inner surface of central passage 312 and the outer surface of guidewire tubular member 310 define an annular inflation/deflation lumen 328 that extends from hub 300 between the outer surface of guidewire tubular member 310 and the inner surface of second outer tubular member 314.

Referring still to FIG. 6, an inflation/deflation tube 316 is secured in an inflation/deflation port 318 is formed in body 302 for providing pressured fluid through hub 300 to a dilation balloon. Inflation/deflation tube 316 may be secured in inflation/deflation port 318 by means of an adhesive or by thermal, ultrasonic or solvent welding. As illustrated, inflation/deflation port 318 is formed at an acute angle to central passage 312 and opens into inflation/deflation lumen 328 distal to the fluid tight seal formed by adhesive 326 between the inside surface of the central passage and guidewire tubular member 310.

A pressure relief port 320 formed in body 302 extends outwardly from inflation/deflation lumen 328 at a location distal to the fluid tight seal formed by adhesive 326 between the inside surface of the central passage and guidewire tubular member 310. In one variation, pressure relief port 320 is essentially identical to pressure relief port 220 of FIGS. 4 and 5. A pressure relief member 322 is secured across pressure relief port 320 to form a fluid tight seal. In one embodiment, a cylindrical retainer 324 is used to secure pressure relief member 322 across pressure relief port 320. Pressure relief member 322 is formed from a material, such as a plastic film, such that the member will rupture or tear when the pressure in inflation/deflation lumen 328 reaches or exceeds a predetermined level. In one variation, the predetermined pressure is equal to or greater than the rated burst pressure of the dilation balloon connected to hub 300.

Referring to FIGS. 3 and 6, it will be appreciated that in the event that a pressure relief member 222 or 322 is ruptured or fails during angioplasty or during stent placement, balloon 108 (FIG. 1) may remain in an inflated or partially inflated condition in a patient's blood vessel. Depending upon the particular situation, it may be difficult or impossible to remove the balloon from the blood vessel without completely deflating the balloon. Further, the blood vessel may remain occluded for longer than desired if the balloon cannot be deflated with the use of negative pressure. This may be particularly problematic in the case of a substantially inelastic non-compliant or semi-compliant balloon since the balloon may not collapse or only partially collapse without the use of negative pressure to aspirate the incompressible fluid from the balloon.

Referring still to FIGS. 3 and 6, pressure relief ports 220 and 320 are located in hubs 200 and 300 at locations where the ports may be rapidly sealed in the event of a rupture of pressure relief members 222 or 322. For example, in the case of a rupture of pressure relief member 222 or 322, a practitioner may place a finger or thumb over the pressure relief port to seal the port and then apply a negative pressure to balloon through the catheter to aspirate the fluid from the balloon. Alternatively, a piece of tape or similar material may be placed over pressure relief ports 220 or 320 to seal the port while the balloon is deflated. Thus, while pressure relief ports 220 and 320, along with relief members 222 and 322 provide a means of preventing over-inflation of dilation balloons during procedures such as angioplasty, the ports may also be rapidly re-sealed to allow for rapid controlled deflation of a dilation balloon in the case of a rupture of the relief member.

While the pressure relief ports and apparatus described above are formed in a wall of a catheter hub, it is contemplated that the ports could be positioned in a wall of the catheter shaft or in an inflation/deflation port connected to the hub. Further, while the pressure relief ports are described in connection with catheters having coaxially configured catheter shafts, the ports may be adapted for use with other types of catheters. Such catheters may have non-coaxial multi-lumen shafts such as extruded dual lumen shafts. Additionally, while the pressure relief apparatus had been described in connection with non-compliant dilation balloons, the apparatus may be used with semi-compliant and complaint balloons.

As will be appreciated, rupture of relief member 222 (FIG. 4) or 322 (FIG. 6) in some cases may result in pressurized fluid contained in inflation/deflation lumen 214 (FIG. 3) or 328 (FIG. 6) and balloon 108 being ejected though pressure relief ports 220 and 320. Thus, in some embodiments, it is desirable to provide means for preventing pressurized fluid from uncontrolled spurting or squirting from ports 220 or 320 into the external environment after a rupture of pressure relief members 222 or 322.

Figure 7A:
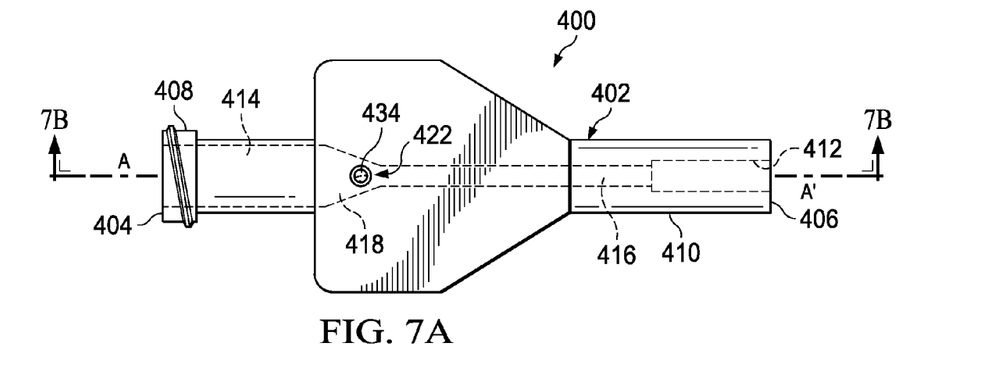
FIG. 7A is a partial top view of a pressure relief apparatus for an inflation/deflation lumen including a splash guard for preventing an uncontrolled release of pressurized fluid through a pressure relief port.
Figure 7B:
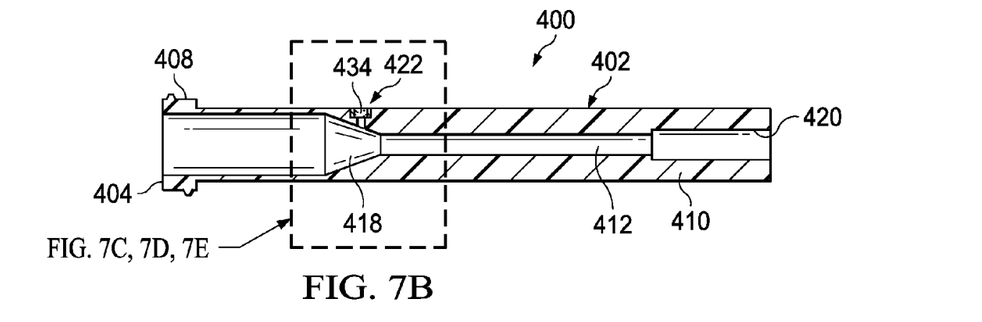
FIG. 7B is a partial lengthwise cross sectional view of the pressure relief apparatus of FIG. 7A.

FIG. 7A is a partial top view of a pressure relief apparatus including a splash guard 434 for preventing an uncontrolled release of pressurized fluid through a pressure relief port 422 formed in a hub 400 of the apparatus. Hub 400 includes a body 402 having a proximal end 404, a distal end 406 and a fitting or connector 408 at proximal end 404 for connecting the hub to a source of pressurized fluid. Hub 400 may be molded from an appropriate plastic such as nylon. In the illustrated embodiment, the connector 408 is a locking female tapered cone luer fitting, for example, a female Luer lock-type fitting such as those sold by Becton Dickinson under the trademark Luer-Lok®. In other embodiments, connector 408 may be a female slip tip-type fitting such as those sold by Becton Dickinson under the trademark Luer-Slip® or another female 6% tapered cone luer connector fitting such as those described in the ISO 594 standard. In still other embodiments, the connector 408 may be a male tapered cone luer fitting, for example, a male Luer lock-type fitting such as a Luer-Lok® fitting, a male slip tip-type fitting such as a Luer-Slip® fitting or another male 6% tapered cone luer connector fitting such as those described in the ISO 594 standard. In yet other embodiments, the connector 408 may be a male or female permanent connector fitting, e.g., a glue-in connector fitting. FIG. 7B is a partial lengthwise cross sectional view of the pressure relief apparatus of FIG. 7A. A generally cylindrical wall 410 defines an inflation/deflation lumen 412 that extends through hub 400 from proximal end 404 to distal end 406 along a longitudinal axis A-A' of the hub. As illustrated, inflation/deflation lumen 412 includes a large diameter proximal portion 414, a small diameter portion 416 and a tapered portion 418 extending between large diameter proximal portion 414 and small diameter portion 416. In one embodiment, a large diameter distal portion 420 of inflation/deflation lumen 412 is configured to receive a pressed or glued in hub extension or catheter shaft (not shown). In the illustrated embodiment, large diameter proximal portion 414 is outwardly tapered toward proximal end 404 from tapered portion 418 and configured to receive a corresponding Luer-type fitting. Distal end 406 may be configured to receive the distal end of a catheter shaft (not shown) connected to hub 400 by means of thermal, solvent or ultrasonic welding, a glue-in connection, a Luer-type fitting or other connection means.

Figure 7C:
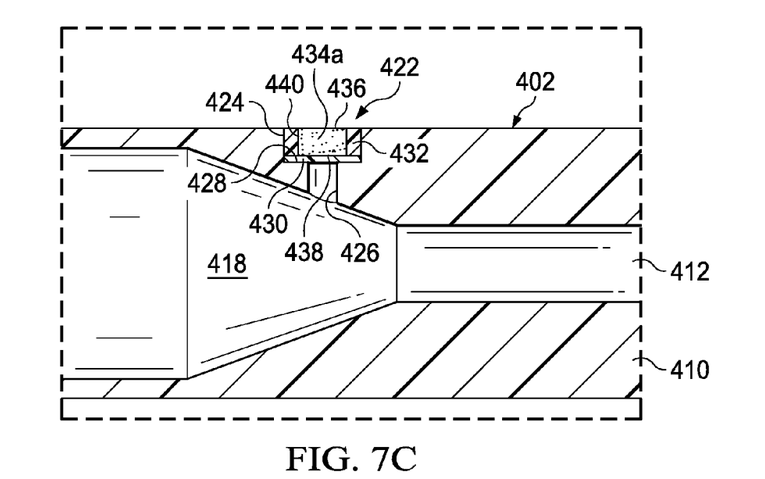
FIGS. 7C, 7D and 7E are enlarged partial cross sectional views of the pressure relief apparatus of FIG. 7A illustrating alternative embodiments of a splash guard.
Figure 7D:
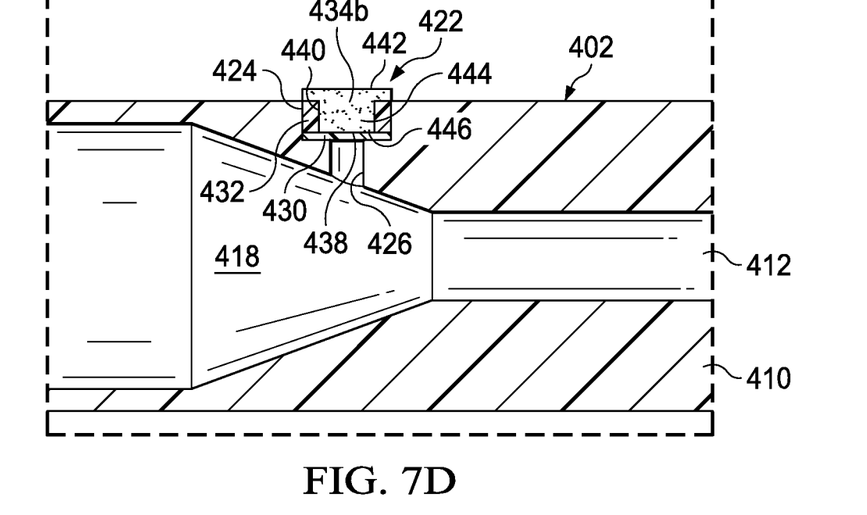
Figure 7E:
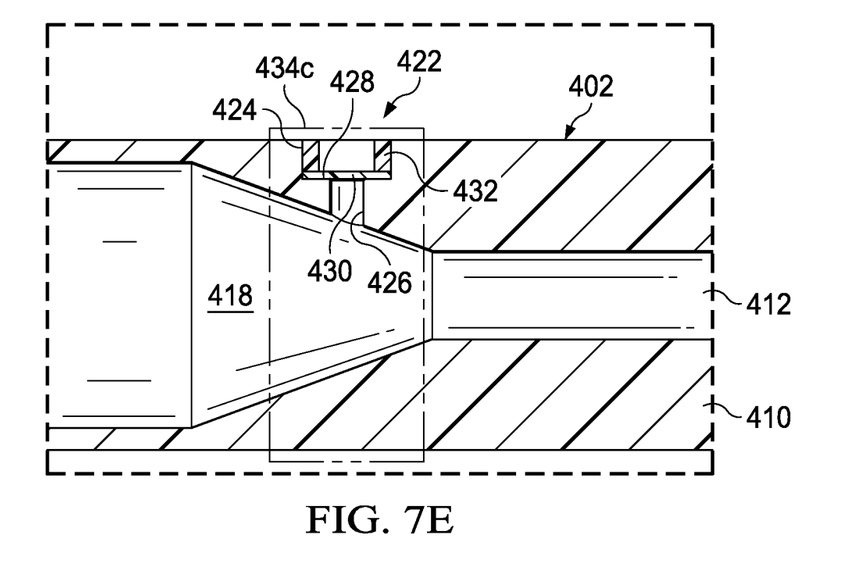

Hub 400 is configured with a pressure relief port 422 that extends through wall 410 and opens into tapered portion 418 of inflation/deflation lumen 412. As illustrated, pressure relief port 422 is perpendicular to longitudinal axis A-A'. FIGS. 7C, 7D and 7E are enlarged cross sectional views of pressure relief port 422 with splash guards 434a, 434b and 434c, respectively. In particular, FIG. 7C is an enlarged cross sectional view of a portion of hub 400 further illustrating a splash guard 434a. As illustrated, relief port 422 includes a generally cylindrical relatively larger diameter, outwardly opening passage 424 and a generally cylindrical relatively smaller, diameter inner passage 426 that opens into the tapered portion inflation/deflation lumen 412. An annular wall 428 extends radially between outwardly opening passage 424 and inner passage 426. A pressure relief member 430 extends across inner passage 426 and annular wall 428. In one embodiment, a cylindrical retaining ring 432 is positioned in outwardly opening passage 424 over pressure relief member 430.

Pressure relief member 430 may be glued to annular wall 428 with an appropriate adhesive, such as a medical grade epoxy, to form a fluid-tight seal across relief port 422. In other embodiments, pressure relief member 430 may be solvent welded or thermally or ultrasonically welded in place. Pressure relief member 430 is selected to fail at a predetermined pressure to release pressure from the inflation/deflation lumen 412 through pressure relief port 422 when the pressure in the inflation/deflation lumen exceeds the predetermined pressure. Pressure relief member 422 may be formed from one or more layers of a suitable plastic film having a tensile strength such that film ruptures or tears when the pressure in inflation/deflation lumen 412 exceeds a predetermined value, for example a selected pressure between 6 and 30 atmospheres. The predetermined pressure value may be approximately equal to the rated burst pressure of a dilation balloon used with a catheter incorporating hub 400. In other variations, the predetermined value may be greater than or less than the rated burst pressure of the balloon.

Referring still to FIG. 7C, splash guard 434a comprises a cylindrical body generally corresponding to geometry of outwardly opening passage 424. Splash guard 434a has an outwardly facing exterior surface 436, an inwardly facing interior surface 438 and a cylindrical side wall 440. Splash guard 434a may be formed from a fluid permeable wire or plastic mesh material or a sheet material perforated, coiled or folded to create a plurality of relatively narrow, (i.e., compared to the dimensions of passages 424, 426) fluid passages extending between inwardly facing interior surface 438 and outwardly facing exterior surface 436. In some materials used for splash guard 434, the fluid passages may be relatively straight from interior surface 438 to exterior surface 436, whereas in other materials the fluid passages may be curved, meandering or interconnected with one another, i.e., forming a network of interconnected passages between the interior and exterior surfaces. In the illustrated embodiment, outwardly facing exterior surface 436 is flush with the exterior surface of body 402 of hub 400 with inwardly facing interior surface 438 positioned against or adjacent to pressure relief member 430. In other embodiments, outwardly facing exterior surface 436 of splash guard 434a may be recessed relative to the exterior surface of body 402 of hub 400 and inwardly facing interior surface 438 may be positioned outwardly from pressure relief member 430.

Pressurized fluid released upon a failure or rupture of pressure relief member 430 flows through generally cylindrical smaller, diameter inner passage 426 and impinges upon splash guard 434a upon entering generally cylindrical enlarged, outwardly opening passage 424 of pressure relief port 422. The pressurized fluid must flow through the plurality of relatively narrow passages to pass through splash guard 434a. Thus, while splash guard 434a permits the flow of pressurized fluid through pressure relief port 422, the narrow passages of the splash guard dissipate a significant fraction of the fluid's pressure by the time the fluid reaches outer surface 436 of the splash guard, thereby preventing the pressurized fluid from taking an unobstructed direct linear path through generally cylindrical enlarged, outwardly opening passage 424 and spurting in an uncontrolled fashion from pressure relief port 422 to the external environment.

FIG. 7D is an enlarged cross sectional view of a portion of hub 400 illustrating a splash guard 434b having an exterior portion 442 extending outwardly from the exterior surface the exterior surface of body 402 of hub 400. Exterior portion 442 of splash guard 434b may be have a circular, rectangular or other geometry and may be formed integrally with an interior portion 444 of the splash guard. As illustrated an interior face or surface 446 is positioned against or adjacent to pressure relief member 430; however, the interior surface may alternatively be positioned outwardly from pressure relief member 430.

Splash guard 434b is similar to splash guard 434a and may be a cylindrical body formed from a fluid permeable wire or plastic mesh material or a sheet material perforated, coiled or folded to create a plurality of relatively narrow fluid passages extending between inwardly facing interior surface 438 and outwardly facing exterior surface 436 of pressure relief port 422. Splash guard 434b functions in the same manner as splash guard 434a to dissipate pressure and thereby prevent an uncontrolled release of pressurized fluid through pressure relief port 422 with exterior portion 442 of splash guard 434b providing additional protection by extending the path that fluid must follow to flow from pressure relief port 422 and increasing the pressure drop across the splash guard. Exterior portion 442 also provides a tactile means of locating pressure relief port 422 in the event of a rupture of pressure relief member 430. For example, in the case of a rupture of pressure relief member 430, a practitioner may place a finger or thumb over exterior portion 442 to seal pressure relief port 422 and then apply a negative pressure to an attached balloon 108 (FIG. 1) through a catheter (not shown) attached to hub 400 to withdraw fluid from the balloon FIG. 7E is an enlarged cross sectional view of a portion of hub 400 illustrating a splash guard 434c illustrated in phantom. Splash guard 434c is formed from a band of a fluid permeable material such as a cloth, mesh, foam or perforated sheet material. It will be understood that a fluid permeable material includes a plurality of relatively narrow fluid passages passing through the material. Splash guard 434c extends circumferentially around the perimeter of hub 400 and may be fastened to the hub with an appropriate adhesive or by means of solvent, thermal or ultrasonic welding. As illustrated, splash guard 434c extends around the entire periphery of hub 400. In different embodiments splash guard 434 may extend only partially around hub 400. Fluid flowing through pressure relief port 422 must flow though splash guard 434c to exit the port. Splash guard 434c thereby prevents the pressurized fluid from taking an unobstructed direct linear path when exiting pressure relief port 422 and spurting in an uncontrolled fashion from the pressure relief port to the external environment.

Figure 8A:
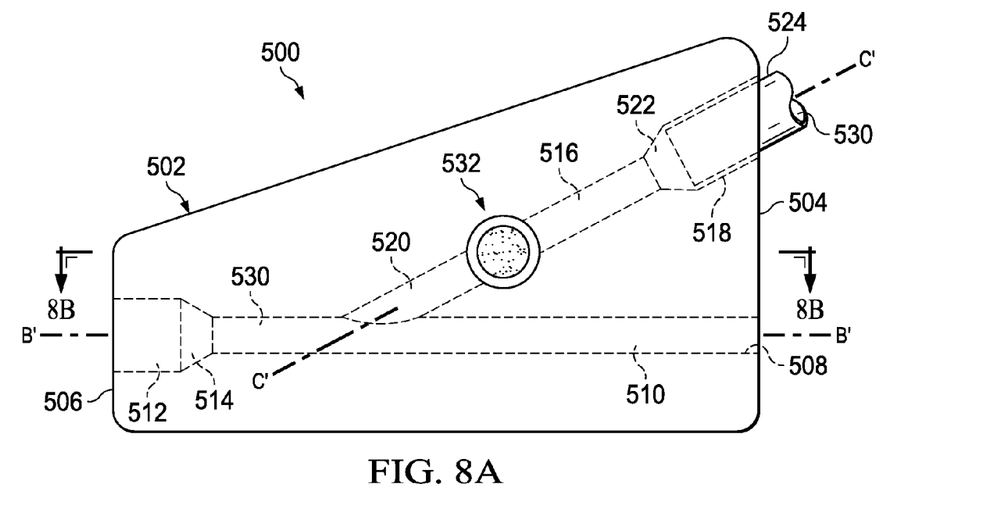
FIG. 8A is a partial cross sectional side view of pressure relief apparatus for a Y-connector hub.
Figure 8B:
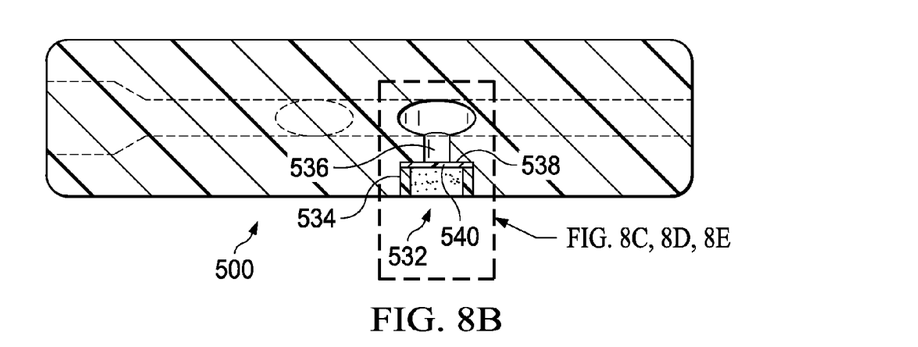
FIG. 8B is a partial cross sectional top view of the Y-connector hub of FIG. 8A.

FIG. 8A is a partial cross sectional side view of a Y-connector hub 500. FIG. 8B is a partial cross sectional top view of Y-connector hub 500. Hub 500 includes a body 502 having a proximal end 504 and distal end 506 with a central lumen 508 extending longitudinally through body 502 along a central longitudinal axis B-B'. Central lumen 508 includes a proximal portion 510, a larger diameter distal portion 512 and a tapered portion 514 that extends between proximal portion 510 and distal portion 512. Large diameter distal portion 512 may be configured to receive a catheter shaft (not shown) therein with a glued or welded connection.

A branch lumen 516 extends at an angle along a second axis C-C' of body 502 intersecting and opening into central lumen 508 midway along the length of body 502 of hub 500. Branch lumen 516 includes a first, proximal portion 518, a distal portion 520 and a tapered portion 522 extending between the proximal and distal portions of branch lumen 516. As illustrated, a tube 524 is received in proximal portion 518 of branch lumen 516. Tube 524 may be connected to hub 500 by means of an appropriate adhesive or by means of solvent, thermal or sonic welding. In different embodiments, central lumen 508 and branch lumen 516 may be provided with connectors, such as Luer-type connectors at the ends thereof to facilitate connection of a catheter shaft and/or pressurization tube to hub 500. For example, female Luer lock-type fitting such as those sold by Becton Dickinson under the trademark Luer-Lok, female slip tip-type fitting such as those sold by Becton Dickinson under the trademark Luer-Slip® or another female 6% tapered cone luer connector fitting such as those described in the ISO 594 standard may be utilized. In still other embodiments, a male tapered cone luer fitting, for example, a male Luer lock-type fitting such as a Luer-Lok® fitting, a male slip tip-type fitting such as a Luer-Slip® fitting or another male 6% tapered cone luer connector fitting such as those described in the ISO 594 standard may be utilized. Tube 524 may be connected to a source of pressurized fluid to inflate a balloon, such as balloon 108 of FIG. 1 attached to hub 500 by means of a catheter shaft (not shown). Central lumen 508, branch lumen 516 and tube 524 thereby form an inflation/deflation lumen 530 that extends though body 502 of hub 500.

Referring to FIG. 8B, a pressure relief port 532 is formed in body 502, extending from distal portion 518 of branch lumen 516 and opening to the exterior of body 502. As illustrated pressure relief port 532 extends perpendicular to axis C-C' of branch lumen 516. Pressure relief port 532 includes a generally cylindrical enlarged, outwardly opening passage 534 and a generally cylindrical smaller, diameter inner passage 536 that opens into distal portion 518 of branch lumen 516. An annular wall 538 extends radially between outwardly opening passage 534 and inner passage 536.

A pressure relief member 540 extends across inner passage 536 and annular wall 538. Pressure relief member 540 may be formed from one or more layers or suitable plastic film having a tensile strength such that film ruptures when the pressure in branch lumen 516 exceeds a predetermined value. Pressure relief member 540 may be may be glued to annular wall 538 with an appropriate adhesive, such as a medical grade epoxy or thermally, ultrasonically or solvent welded in place to form a fluid tight seal across pressure relief port 532. In one embodiment, a cylindrical retaining ring 542 may be may be welded or glued in place in outwardly opening passage 534 over pressure relief member 540 to aid in retaining the pressure relief member in position. A splash guard 542 is positioned across pressure relief port 532 for preventing a linear uncontrolled release of pressurized fluid through the pressure relief port.

Figure 8C:
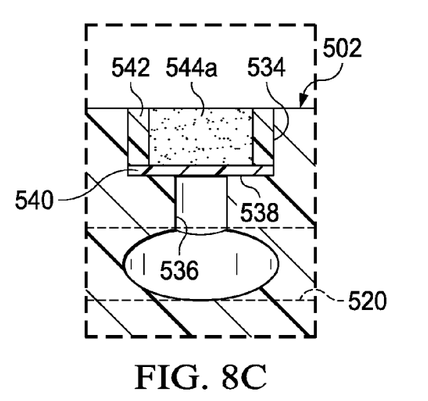
FIGS. 8C, 8D and 8E are enlarged partial cross sectional views of the Y-connector hub of FIG. 8A illustrating alternative embodiments of a splash guard.
Figure 8D:
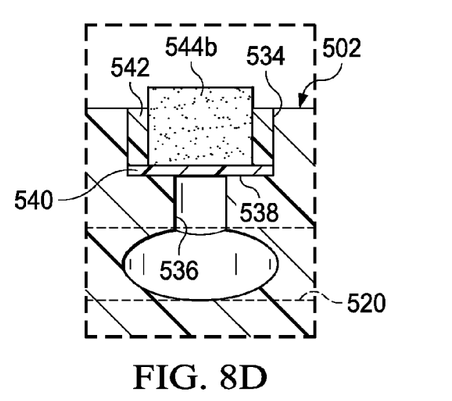
Figures 8E, 9:
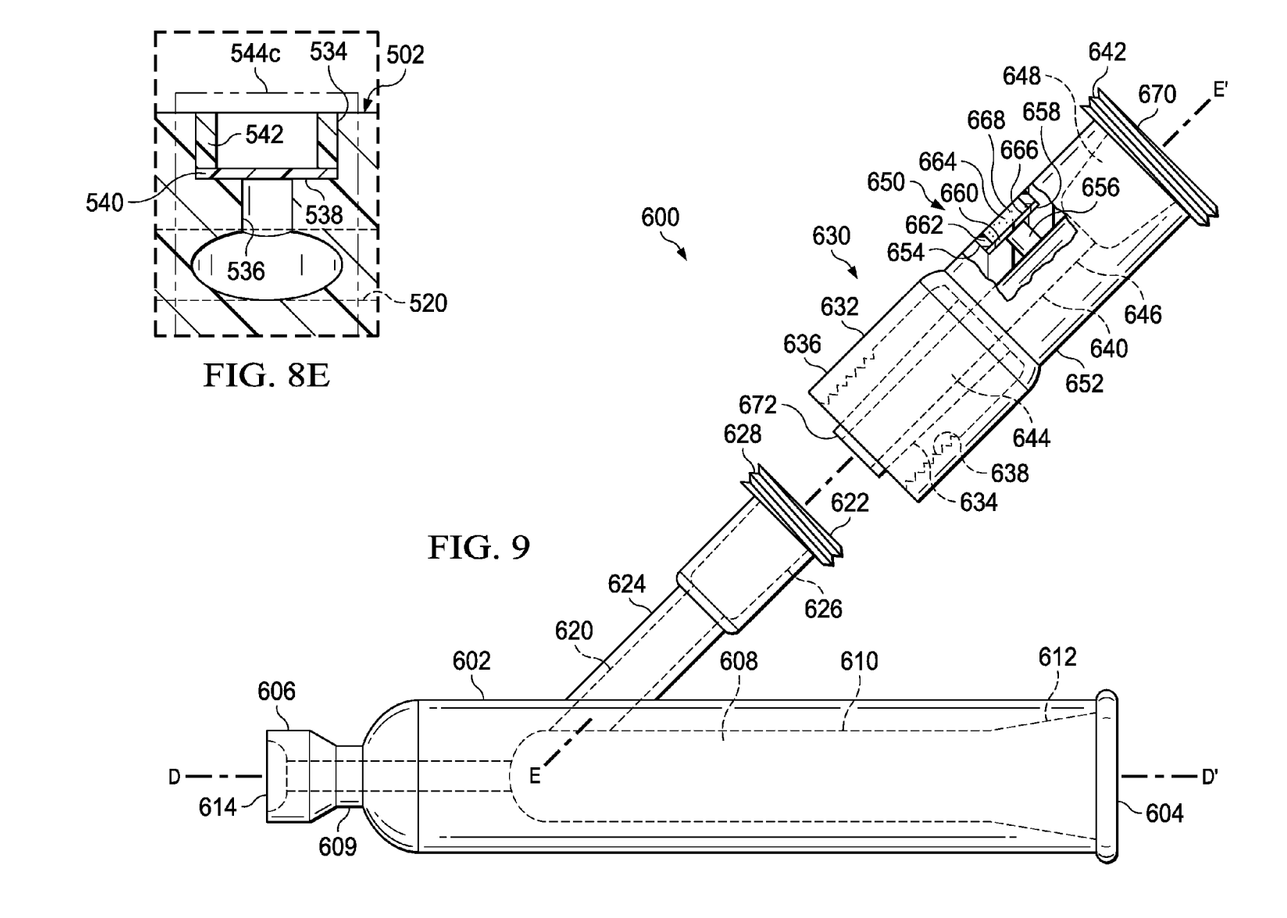
FIG. 9 is a partial cross sectional side view of a Y-connector hub including an extension with a pressure relief port and splash guard.

FIGS. 8C, 8D and 8E are enlarged cross sectional views of pressure relief port 532 with splash guards 544a, 544b and 544c, respectively. Splash guards 544a-544c are substantially identical to, and function in the same manner as splash guards 434a-434c of FIGS. 7C-7E.

FIG. 9 is a partial cross sectional side view of a Y-connector hub 600 with removable extension 630. Hub 600 has a substantially cylindrical wall 602 with a proximal end 604 and a distal end 606. Cylindrical wall 602 defines central lumen 608 extending along a central axis D-D' between the proximal end 604 and distal end 606. Central lumen 608 has a large diameter proximal portion 610 with an outwardly taped end section 612 that may be configured to receive a male Leur-type fitting or an end of a tubular member (not shown) secured in tapered section 612 with an appropriate adhesive or by means of solvent, thermal or ultrasonic welding. Central lumen 608 includes a narrow diameter distal portion 609 extending from a distal end of large diameter portion 610 to distal end 606 of cylindrical wall 602 with a enlarged end portion 614. End portion 614 may be configured to receive the proximal end of a tubular member such as a catheter shaft with a glued or welded connection and/or provided with a connector such as a Leur-type fitting.

Y-connector hub 600 includes a branch lumen 620 extending from a proximal end 622 through hub 600 and opening into large diameter proximal portion 610 of central lumen 608 midway along the length of the hub. An angled cylindrical wall 624 defines a portion of branch lumen 620 that extends from cylindrical wall 602 along an axis E-E' that intersects axis D-D' at an acute angle. As illustrated, proximal end 622 of angled cylindrical wall 624 includes a externally threaded female Leur-type connection 628 with an outwardly tapered portion 626 of branch lumen 620 for receiving a corresponding male Leur-type fitting 632 at the distal end of a removable extension 630 of branch lumen 620.

Leur-type fitting 632 of extension 630 includes a male insert 634 and a collar 636 with internal threads 638 for securing fitting 632 to connector 628. A passage 644 extends though extension 630 from distal end 638 to proximal end 640 of the extension with a female Leur-type connection 642 at the proximal end of the extension. Passage 640 includes a narrow diameter distal portion 646 that opens into a tapered, larger diameter proximal end portion 648 which is configured to receive a male luer-type fitting. When extension 630 is connected to angled cylindrical wall 624 of hub 600, central lumen 610, branch lumen 620 and passage 644 are in fluid communication and provide a fluid path through extension 630 and hub 600. In different embodiments, larger diameter proximal end portion 648 may be configured to receive an end of a tubular member secured therein with an appropriate adhesive or by welding.

Extension 630 is configured for attachment to a source of pressurized fluid for inflating a balloon such as balloon 108 of FIG. 1 connected to a catheter shaft (not shown) connected in turn to distal end 606 of hub 600. Central lumen 608, branch lumen 620 and passage 640 thereby form an inflation/deflation lumen for inflating and deflating a balloon connected to a catheter shaft (not shown) connected in turn to distal end 606 of hub 600 for passage of pressurized fluid therethrough.

In different embodiments, hub 600 and extension 630 may be provided with female Luer lock-type fitting such as those sold by Becton Dickinson under the trademark Luer-Lok, female slip tip-type fitting such as those sold by Becton Dickinson under the trademark Luer-Slip® or another female 6% tapered cone luer connector fitting such as those described in the ISO 594 standard. Hub 600 and extension 630 may also be provided a male tapered cone luer fittings, such as a male Luer lock-type fitting such as a Luer-Lok® fitting, a male slip tip-type fitting such as a Luer-Slip® fitting or another male 6% tapered cone luer connector fitting such as those described in the ISO 594. In the illustrated embodiment, extension 630 defines a fluid inlet port 670 configured with a female tapered cone luer fitting and a fluid outlet port 672 configured with a male tapered cone luer fitting.

A pressure relief port 650 is formed in a cylindrical sidewall 652 of extension 630, extending though the sidewall to narrow diameter distal portion 646 of passage 644. Pressure relief port 650 is positioned perpendicular to axis E-E' and includes a generally cylindrical enlarged, outwardly opening passage 654 and a generally cylindrical smaller, diameter inner passage 656 that opens into the narrow diameter distal portion 646 of passage 644. An annular wall 658 extends radially between outwardly opening passage 654 and inner passage 656. A pressure relief member 660 extends across inner passage 656 and annular wall 658. Pressure relief member 660 may be formed from one or more layers of a film or sheet material selected to rupture or fail at a predetermined pressure. The predetermined pressure value may be greater than, less than or approximately equal to the rated burst pressure of a dilation balloon used with a catheter apparatus incorporating 600. Pressure relief member 660 may be glued with an appropriate adhesive, such as a medical grade epoxy, to annular wall 658 to form a fluid-tight seal across relief port 650. Alternatively, pressure relief member 660 may be solvent, thermally or ultrasonically welded to annular wall 658. A cylindrical retaining ring 662 may be positioned in outwardly opening passage 654 over pressure relief member 660, retaining the pressure relief member between annular wall 658 and the retaining ring. Retaining ring 662 may be glued or welded in place in enlarged, outwardly opening passage 654 of pressure relief port 650.

In the embodiment illustrated in FIG. 9, a splash guard 664 is positioned in pressure relief port 650. Splash guard 664 comprises a cylindrical body generally corresponding to the geometry of generally cylindrical enlarged, outwardly opening passage 654 of the pressure relief port. Splash guard 664 may be formed from a fluid permeable wire or plastic mesh material or a sheet material perforated, coiled or folded to create a plurality of relatively narrow fluid passages extending between inwardly facing interior surface 666 and outwardly facing exterior surface 668 of the splash guard. As illustrated, outwardly facing exterior surface 668 is flush with the exterior surface extension 630 with inwardly facing interior surface 666 positioned against or adjacent to pressure relief member 660. In other embodiments, outwardly facing exterior surface 668 of splash guard 664 may be recessed or elevated relative to the exterior surface of extension 630 and inwardly facing interior surface 666 may be positioned outwardly from pressure relief member 660. In still other embodiments, extension 630 includes a pressure relief port 650 without splash guard 664.

Pressurized fluid released upon a failure or rupture of pressure relief member 660 flows through generally cylindrical smaller, diameter inner passage 656 and impinges upon splash guard 664 upon entering generally cylindrical enlarged, outwardly opening passage 654 of pressure relief port 650. Splash guard 664 obstructs the flow of fluid though pressure relief port 650 and increases the pressure drop across the relief port thereby preventing fluid flowing through the port from taking an unobstructed linear path through the port and spurting into the external environment. In different embodiments, splash guard 664 may be substantially identical to, and function in the same manner as splash guards 434a-434c of FIGS. 7C-7E.

Figure 10A:
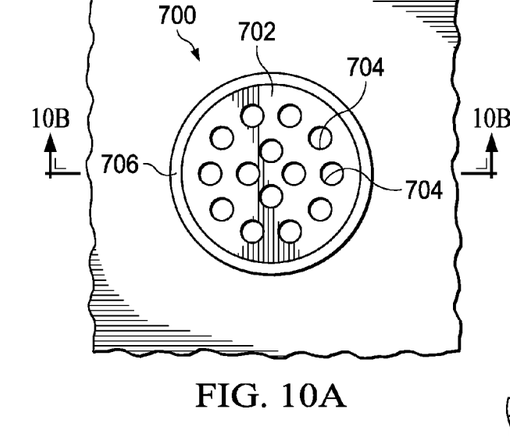
FIG. 10A is a partial top view illustrating an alternate embodiment of a splash guard.
Figure 10B:
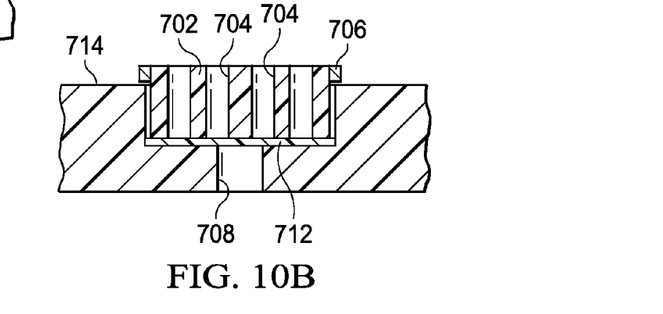
FIG. 10B is a partial side sectional view of the splash guard of FIG. 10A.

FIG. 10A is a partial top view of an alternate embodiment of a splash guard 700. FIG. 10B is a partial side sectional view of the splash guard of FIG. 10A positioned in a pressure relief port 708 substantially identical to pressure relief ports 422, 532 and 660 of FIGS. 7-9. Splash guard 700 is formed from one or more layers of a perforated sheet material 702 such as a plastic or metal sheet. Splash guard 700 may include a rim or ring 706 extending around the periphery of sheet 702 configured to rest on or be attached to the exterior surface of a tube 714 such as extension 630 (FIG. 9) or hub, such as hub 400 (FIG. 7) that defines an inflation/deflation lumen. In other embodiments, perforated sheet 702 may be formed integrally with pressure relief port 708 and tube 714 by means of molding or machining.

Pressurized fluid flowing through pressure relief port 708 must pass through perforations 704 which form multiple, relatively narrow, fluid flow channels through splash guard 700 which increases the pressure drop across the splash guard, slowing the rate of fluid flow. Splash guard 700 thereby prevents unobstructed flow though pressure relief port 708 which could result in an uncontrolled spray, stream or spurt of fluid from the port in the event of a failure or rupture of pressure relief member 712.

Figure 11A:
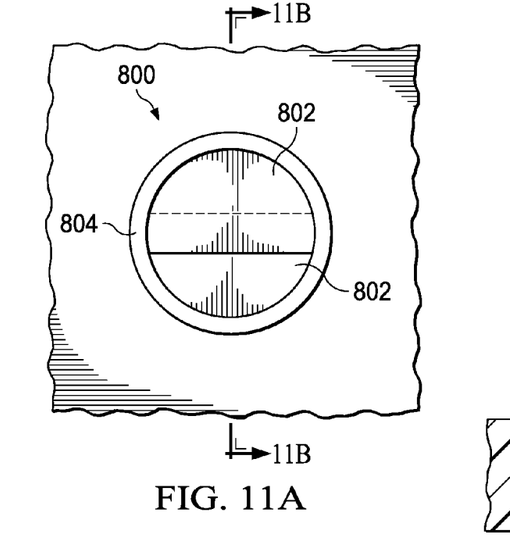
FIG. 11A is a partial top view of an embodiment of a second alternative splash guard; and, FIG. 11B is a partial side sectional view of the splash guard of FIG. 11A.
Figure 11B:
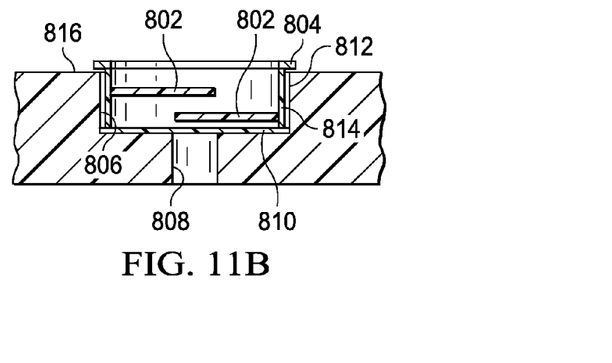

FIG. 11A is a partial top view of an embodiment of a second alternative splash guard 800. FIG. 11B is a partial side sectional view of the splash guard of FIG. 11A positioned in a pressure relief port 808 substantially identical to pressure relief ports 422, 532 and 660 of FIGS. 7-9 including a pressure relief member 810. Splash guard 800 may include a rim or ring 804 extending around the periphery of a cylindrical sidewall 814 of the splash guard. Ring 804 is configured to rest on or be attached to the exterior surface of a tube 816 such as extension 630 (FIG. 9) or hub, such as hub 400 (FIG. 7) that defines an inflation/deflation lumen.

Splash guard 800 includes one or more baffles 802 positioned in pressure relief port 808 that partially obstruct the pressure relief port to form a labyrinth of relatively narrow flow passages. As illustrated, baffles 802 extend perpendicular from a cylindrical sidewall 814 of splash guard 800 such that fluid passing through pressure relief port 808 must flow around baffles 802 which diverts the flow of the fluid though pressure relief port 808 and increases the pressure drop across the pressure relief port. Splash guard 800 may be formed from a suitable plastic material such as nylon. In different embodiments, baffles 802 may be formed integrally with pressure relief port 808 and tube 816 by means of molding or machining in which case, the baffles would be positioned perpendicular to sidewall 806 of pressure relief port 808. Baffles 802 of splash guard 800 change the direction of flow of a fluid flowing though pressure relief port 808 at least twice, thereby slowing the flow and preventing direct linear flow though the pressure relief port that may result in an uncontrolled spray, stream or spurt of fluid from the port in the event of a failure or rupture of pressure relief member 810.

It will be appreciated by those skilled in the art having the benefit of this disclosure that this balloon catheter pressure relief valve provides a means of preventing over-pressurization of a dilation catheter balloon. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A pressure relief apparatus for a balloon dilation catheter including an inflation/deflation lumen for inflating and deflating the balloon comprising:
    a pressure relief port formed through a wall of the inflation/deflation lumen, the pressure relief port including a first outwardly opening passage and a second passage in fluid communication with the first passage and extending inwardly from the first passage and opening into the inflation/deflation lumen, and wherein the cross-sectional area of the first passage is larger than the cross-sectional area of the second passage;
    a pressure relief member secured across the pressure relief port in the wall of the inflation/deflation lumen to form a fluid tight seal, enabling inflation of the dilation balloon with a substantially incompressible fluid provided through the inflation/deflation lumen wherein the fluid tight seal formed by the pressure relief member fails when the pressure in the inflation/deflation lumen exceeds a predetermined pressure; and
    a splash guard positioned across the pressure relief port, the splash guard formed from a fluid permeable body defining a plurality of flow passages therethrough, the cross-sectional area of each of the flow passages being narrow relative to the cross-sectional area of the first and second passages such that fluid released from the inflation/deflation lumen upon failure of the pressure relief member flows through the flow passages of the splash guard whereby the splash guard partially obstructs fluid flow through the pressure relief port to prevent a direct uncontrolled release of the fluid through the pressure relief port, the fluid flowing through the splash guard to release pressure from the inflation/deflation lumen.

2. The pressure relief apparatus of claim 1 wherein the pressure relief member comprises a fluid permeable body formed from a plastic or metal mesh material, and wherein the splash guard is positioned inside the pressure relief port.

3. The pressure relief apparatus of claim 1 wherein the pressure relief member comprises a fluid permeable body formed from a plastic or metal mesh material, and wherein the splash guard is positioned inside the pressure relief port with a portion thereof extending outwardly from the pressure relief port.

4. The pressure relief apparatus of claim 1 wherein the pressure relief member comprises a fluid permeable fabric material extending around at least a portion of the periphery of the wall of the inflation/deflation lumen and over the pressure relief member.

5. The pressure relief apparatus of claim 1 wherein the splash guard comprises at least one perforated sheet extending across the pressure relief port.

6. The pressure relief apparatus of claim 1 further comprising:
    a wall extending between an inside end of the first passage of the pressure relief port and an outside end of the second passage of the pressure relief port; and
    wherein the pressure relief member is disposed adjacent the wall and across the outside end of the second passage of the pressure relief port, the pressure relief member blocking the pressure relief port.

7. The pressure relief apparatus of claim 6 further comprising a retainer for retaining the pressure relief member in the pressure relief port, the pressure relief member and retainer forming a fluid tight seal across the pressure relief port.

8. The pressure relief apparatus of claim 1 further comprising a hub wherein the pressure relief port is formed in the hub.

9. The pressure relief apparatus of claim 1 wherein the predetermined pressure is equal to or greater than the rated burst pressure of the dilation balloon.

10. The pressure relief apparatus of claim 1 wherein the pressure relief member is a plastic film.

11. A pressure relief apparatus for a balloon dilation catheter including a shaft having a dilation balloon attached to the distal end of the shaft and an inflation/deflation lumen for inflating and deflating the balloon comprising:
- a pressure relief port formed through the wall of the inflation/deflation lumen wherein fluid enters and leaves the inflation/deflation lumen via an inflation/deflation port and wherein the pressure relief port further comprises a first outwardly opening passage and a second passage in fluid communication with the first passage and extending inwardly from the first passage and opening into the inflation/deflation lumen, and wherein the cross-sectional area of the first passage is larger than the cross-sectional area of the second passage;
- a pressure relief member secured across the pressure relief port in the wall of the inflation/deflation lumen to form a fluid tight seal, enabling inflation of the dilation balloon with a substantially incompressible fluid provided through the inflation/deflation lumen and wherein the pressure relief member is operative to fail during inflation of the balloon when the pressure in the inflation/deflation lumen exceeds a predetermined pressure and releases fluid through the pressure relief port; and
- a splash guard positioned across the pressure relief port, the splash guard formed from a fluid permeable body defining a plurality of flow passages therethrough, the cross-sectional area of each of the flow passages being narrow relative to the cross-sectional area of the first and second passages such that fluid released from the inflation/deflation lumen upon failure of the pressure relief member flows through the flow passages of the splash guard whereby the splash guard prevents a direct uncontrolled release of the fluid through the pressure relief port when fluid flows through the pressure relief port to release pressure from the inflation/deflation lumen.

12. The pressure relief apparatus of claim 11 wherein the pressure relief member comprises a fluid permeable body formed from a plastic or metal mesh material, and wherein the splash guard is positioned inside the pressure relief port.

13. The pressure relief apparatus of claim 11 wherein the pressure relief member comprises a fluid permeable body formed from a plastic or metal mesh material, and wherein the splash guard is positioned inside the pressure relief port with a portion thereof extending outwardly from the pressure relief port.

14. The pressure relief apparatus of claim 11 wherein the pressure relief member comprises a fluid permeable fabric material extending around at least a portion of the periphery of the wall of the inflation/deflation lumen and over the pressure relief member.

15. The pressure relief apparatus of claim 11 wherein the splash guard comprises at least one perforated sheet extending across the pressure relief port.

16. The pressure relief apparatus of claim 11 wherein the pressure relief port comprises:
- a first outwardly opening passage having an outer end and a second passage in fluid communication with the first passage and extending inwardly from the first passage and opening into the inflation/deflation lumen and wherein the cross-sectional area of the first passage is larger than the cross-sectional area of the second passage; and
- a wall extending radially between an inside end of the first passage of the pressure relief port and an outside end of the second passage of the pressure relief port.

17. The pressure relief apparatus of claim 16 wherein the pressure relief member is disposed adjacent the wall and across the outermost end of the second passage of the pressure relief port.

18. The pressure relief apparatus of claim 11 further comprising a hub having a body defining the inflation/deflation port and the pressure relief port.

19. A pressure relief apparatus for a balloon dilation catheter including an inflation/deflation lumen for inflating and deflating the balloon comprising:
- an extension of the inflation/deflation lumen having a fluid inlet port and a fluid outlet port with a pressure relief port formed through a wall of the inflation/deflation lumen, the pressure relief port including a first outwardly opening passage and a second passage in fluid communication with the first passage and extending inwardly from the first passage and opening into the inflation/deflation lumen, and wherein the cross-sectional area of the first passage is larger than the cross-sectional area of the second passage;
- an interior wall extending radially between an inside end of the first passage of the pressure relief port and an outside end of the second passage of the pressure relief port
- a pressure relief member secured to the interior wall and extending across the pressure relief port to form a fluid tight seal enabling inflation of the dilation balloon with a substantially incompressible fluid provided through the inflation/deflation lumen wherein the fluid tight seal formed by the pressure relief member fails when the pressure in the inflation/deflation lumen exceeds a predetermined pressure; and
- wherein one of the fluid inlet port and fluid outlet port is configured with a male tapered cone fitting and the other of the fluid inlet port or fluid outlet port is configured with a female tapered cone fitting; and
- further comprising a splash guard positioned across the pressure relief port, the splash guard formed from a fluid permeable body defining a plurality of flow passages therethrough, the cross-sectional area of each of the flow passages being narrow relative to the cross-sectional area of the first and second passages such that fluid released from the inflation/deflation lumen upon failure of the pressure relief member flows through the flow passages of the splash guard whereby the splash guard partially obstructs fluid flow through the pressure.

* * * * *